US005869482A

United States Patent [19]

Proudfoot et al.

[11] Patent Number: 5,869,482

[45] Date of Patent: Feb. 9, 1999

[54] DIPYRIDIO[2,3-B:3',2'-] AZEPINES AND THEIR USE IN THE PREVENTION OR TREATMENT OF HIV INFECTION

[75] Inventors: John R. Proudfoot, Newton, Conn.; Alexey B. Dyatkin, Lansdale, Pa.

[73] Assignee: Boehringer Ingelheim Pharmacueticals, Inc., Ridgefield, Conn.

[21] Appl. No.: 953,564

[22] Filed: Oct. 17, 1997

Related U.S. Application Data

[60] Provisional application No. 60/030,375 Nov. 6, 1996.

[51] Int. Cl. 6 ........................ A61K 31/55; C07D 487/00; C07D 498/00; C07D 513/00

[52] U.S. Cl. ........................... 514/215; 514/217; 540/578

[58] Field of Search ............................ 540/578; 514/215, 514/217

[56] References Cited

U.S. PATENT DOCUMENTS 5,366,972 11/1994 Hargrave et al. ....................... 514/220

*Primary Examiner*—Richard L. Raymond
*Assistant Examiner*—Bruck Kifle
*Attorney, Agent, or Firm*—Robert P. Raymond; Alan R. Stempel; Mary-Ellen Devlin

[57] ABSTRACT

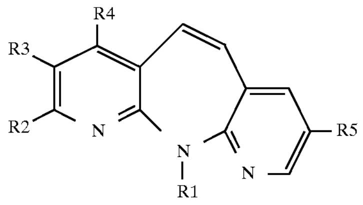

Disclosed are novel dipyridoazepines useful in the prevention or treatment of HIV infection. Exemplary compounds are 11-Ethyl-dipyrido[2,3-b:3',2'-f]azepine and 11-Cyclopropyldipyrido[2,3-b:3',2'-f]azepine.

6 Claims, No Drawings

DIPYRIDIO[2,3-B:3',2'-] AZEPINES AND THEIR USE IN THE PREVENTION OR TREATMENT OF HIV INFECTION

CROSS-REFERENCES TO RELATED APPLICATIONS

The benefit of provisional application Ser. No. 60/030,375, filed on Nov. 6, 1996, is hereby claimed.

FIELD OF THE INVENTION

The invention relates to novel dipyrido[2,3-b:3',2'-f] azepines and pharmaceutically acceptable salts thereof, methods for preparing these compounds, the use of these compounds either alone or in combination with other anti-virals, immunomodulators, antibiotics, anti-infectives, or vaccines in the prevention or treatment of HIV infection, and to pharmaceutical compositions containing these compounds.

BACKGROUND OF THE INVENTION

The human disease, Acquired Immune Deficiency Syndrome (AIDS), is caused by the Human Immunodeficiency Virus (HIV), particularly the strain known as HIV-1.

Like other viruses, HIV-1 cannot replicate without commandeering the biosynthetic apparatus of the host cell it infects. It causes this apparatus to produce the structural proteins which make up the viral progeny. These proteins are coded for by the genetic material contained within the infecting virus particle, or virion. Being a retrovirus, however, the genetic material of HIV is RNA, not DNA as in the host cell's genome. Accordingly, the viral RNA must first be converted into DNA, and then integrated into the host cell's genome, in order for the host cell to produce the required viral proteins. The conversion of the RNA to DNA is accomplished by the enzyme reverse transcriptase (RT), which along with the RNA is a component of the infecting virion. Reverse transcriptase has three known enzymatic functions; it acts as an RNA-dependent DNA polymerase, as a ribonuclease, and as a DNA-dependent DNA polymerase. Acting first as an RNA-dependent DNA polymerase, RT makes a single-stranded DNA copy of the viral RNA. Acting as a ribonuclease, RT frees the DNA just produced from the original viral RNA and destroys the original RNA. Finally, acting as a DNA-dependent DNA polymerase, RT makes a second, complementary DNA strand, using the first DNA strand as a template. The two strands form double-stranded DNA, which is integrated into the host cell's genome by another enzyme called integrase.

Compounds which inhibit the enzymatic functions of HIV-1 reverse transcriptase will inhibit replication of HIV-1 in infected cells.

A number of compounds that inhibit the enzymatic functions of HIV-1 reverse transcriptase are known. One class of known HIV-1 RT inhibitors is the nucleoside analogs. This class includes 3'-azido-3'-deoxythymidine (AZT), 2',3'-dideoxyinosine (ddI), and 2',3'-dideoxycytidine (ddC). Another class is the non-nucleoside analogs. This class includes, inter alia, nevirapine, which is 11-cyclopropyl-5,11-dihydro-4-methyl-6H-dipyrido[3,2-b:2',3'-e][1,4] diazepin-6-one. Nevirapine and other paricularly relevant compounds of the non-nucleoside class are described in U.S. Pat. No. 5,366,972; and by Hargrave et al., "Novel Non-Nucleoside Inhibitors of HIV-1 Reverse Transcriptase. 1. Tricyclic Pyridobenzo- and Dipyridodiazepinones", *J. Med. Chem.* 34, 2231 (1991).

OBJECT OF THE INVENTION

As with any anti-viral therapy, use of RT inhibitors in the treatment of AIDS eventually leads to virus which is less sensitive to the given drug. Resistance (reduced sensitivity) to these drugs is the result of mutations which occur in the reverse transcriptase segment of the pol gene.

The object of the present invention is to provide improved, non-nucleoside inhibitors of HIV-1 RT which are more potent against mutant strains of HIV-1 than the known compounds of this class.

The compounds of the present invention satisfy this object in that they are highly potent against not only the wild-type (non-mutated) virus RT enzyme, but are also effective against the reverse transcriptase of many mutant viruses which have been observed in patients who have been treated with RT inhibitors. Specifically, the compounds of the present invention are effective in inhibiting the Y181C mutant [in which the tyrosine (Y) at codon 181 has been mutated to a cysteine (C) residue] which has been the most commonly observed mutant in clinical studies following therapy with many non-nucleoside reverse transcriptase inhibitors. The compounds are also effective against other observed mutant enzymes which contain a single point mutation such as Y188L, K103N, V106A, G190A, Y188C, or P236L.

SUMMARY OF THE INVENTION

A first aspect of the invention comprises novel dipyrido [2,3-b:3',2'-f]azepines. These possess inhibitory activity against both wild-type and mutant HIV-1 RT. A second aspect of the invention comprises methods for making these novel compounds. A third aspect of the invention is a method for preventing or treating HIV-1 infection which comprises administering, to a human being exposed to or infected by HIV-1, a prophylactcally or therapeutically effective amount of one of the above-mentioned novel compounds, either alone or in combination with other anti-viral agents, immunomodulators, antibiotics, anti-infectives, or vaccines. A final aspect of the invention comprises pharmaceutical compositions suitable for the prevention or treatment of HIV-1 infection comprising the above-mentioned compounds.

DESCRIPTION OF THE INVENTION

In one of its composition of matter aspects, the invention comprises dipyrido[2,3-b:3',2'-f]azepines of the formula I

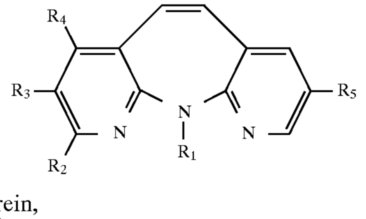

I wherein, $R^1$ is hydrogen, alkyl of 1 to 4 carbon atoms, fluoroalkyl of 1 to 4 carbon atoms and 1 to 3 fluorine atoms, cycloalkyl of 3 to 6 carbon atoms, oxetanyl, thietanyl, tetrahydrofuranyl, tetrahydrothienyl, tetrahydropyranyl, tetrahydrothiopyranyl, alkenylmethyl or alkynylmethyl of 3 to 4 carbon atoms, alkyloxyalkyl or alkylthioalkyl of 2 to 3 carbon atoms, alkanoyl or alkyl(thio)carbonyl of 2 to 5 carbon atoms, cyano, cyanoalkyl of 2 to 3 carbon atoms;

$R^2$ is a hydrogen atom, alkyl of 1 to 6 carbon atoms, cycloalkyl of 3 to 6 carbon atoms, alkenyl or alkynyl of 2 to 6 carbon atoms, trihalomethyl, hydroxyalkyl of 1 to 6 carbon atoms, alkyloxy or alkylthio of 2 to 6 carbon atoms, alkyloxyalkyl or alkylthioalkyl of 2 to 6 carbon atoms, pyrrolidinyl, pyrrolinyl, piperidinyl, mono- or di-alkylamino wherein each alkyl moiety contains 1 to 3 carbon atoms, halogen, cyano, nitro, or carboxyl, aryl (wherein aryl is phenyl, pyridinyl, thienyl, furanyl, pyrrolyl, imidazolyl, pyrazolyl, oxazolyl, isoxazolyl, thiazolyl or isothiazolyl) which is either unsubstituted or substituted by hydroxyl, amino, halogen, alkyl or alkyloxy of 1 to 3 carbon atoms;

$R^3$ is a hydrogen atom, methyl or halogen;

$R^4$ is a hydrogen atom, methyl, ethyl or halogen; and, $R^5$ is a hydrogen atom, hydroxy, amino, hydroxymethyl or aminomethyl.

A subgeneric aspect of the invention comprises compounds of formula I wherein $R^1$ is alkyl of 1 to 3 carbon atoms or cycloalkyl of 3 to 4 carbon atoms;

$R^2$ is a hydrogen atom, methyl, trihalomethyl, methoxy, pyrolidinyl, pyrrolinyl, piperidinyl, dimethylamino, halogen, cyano, nitro or aryl (wherein aryl is phenyl, pyridinyl, thienyl, furanyl, pyrrolyl, imidazolyl, pyrazolyl, oxazolyl, isoxazolyl, thiazolyl or isothiazolyl) which is either unsubstituted or substituted by methyl, methoxy, hydroxyl, amino, or halogen;

$R^3$ is a hydrogen atom, methyl, chloro or bromo;

$R^4$ is hydrogen or methyl; and, $R^5$ is a hydrogen atom.

A particular subgeneric aspect of the invention comprises compounds of formula I wherein, $R^1$ is ethyl or cyclopropyl;

$R^2$ is hydrogen, chloro, or pyrazolyl; and, $R^3$, $R^4$, $R^5$ are hydrogen

Preferred compounds of formula I are:

11-Ethyl-dipyrido[2,3-b:3',2'-f]azepine, and

11-Cyclopropyl-dipyrido[2,3-b:3',2'-f]azepine.

The invention also comprises pharmaceutically acceptable salts of the above-described compounds.

Compounds of formula I wherein $R^1$ through $R^5$ are as defined above, may be obtained by cyclizing compounds of formula II

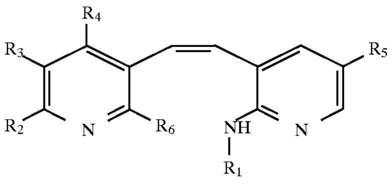

II wherein $R^1$ through $R^5$ are as defined above, and $R^6$ is a leaving group, for instance fluoro, chloro, bromo, or alkoxy.

These reactions are generally carried out under an inert atmosphere of argon or nitrogen, and in inert solvents such as 1,4-dioxane or tetrahydrofuran and the like, at temperatures generally between room temperature and the boiling point of the solvent in the presence of a base such as sodium hydride or sodium hexamethyldisilazide.

Compounds of formula II above wherein $R^1$ through $R^6$ are as defined above, may be obtained from compounds of formula III

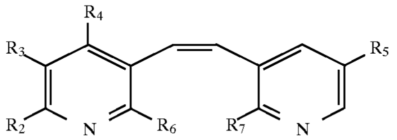

III wherein $R^2$ through $R^6$ are as defined above and $R^7$ is fluoro, chloro or bromo, by reaction with a compound of formula IV $R^1$—$NH_2$ IV wherein $R^1$ is defined above. These reactions are generally carried out in an inert solvent such as 1,4-dioxane or tetrahydrofuran and the like generally between room temperature and the boiling point of the solvent. In cases where the boiling point of IV is lower than the boiling point of the solvent it may be advantageous to carry out the reaction in a closed vessel.

In some cases the reaction of compounds of formula III with compounds of formula IV will give directly compounds of formula I above.

Compounds of formula III wherein and $R^2$ through $R^7$ are as defined above, may be obtained from compounds of formula V

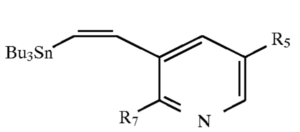

V wherein $R^5$ and $R^7$ are as defined above by reaction with a compound of formula VI

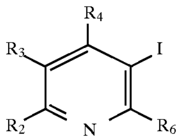

VI wherein $R^2$, $R^3$, $R^4$ and $R^6$ are as defined above. These reactions are generally carried out in an inert solvent such as tetrahydrofuran, dioxane, dimethylformamide or N-methylpyrrolidinone at a temperature between room temperature and the boiling point of the solvent in the presence of a catalyst such as $Pd(Ph_3P)_2Cl_2$ or $Pd(Ph_3P)_4$ or $Pd(Ph_3As)_4$.

Compounds of formula V may be obtained from compounds of formula VII

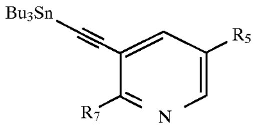

VII wherein $R^5$ and $R^7$ are as defined above, by reaction with dicyclopentadienylchlorozirconium hydride in an inert solvent such as tetrahydrofuran followed by hydrolysis with, for example, silica gel.

Compounds of formula VII may be obtained from compounds of formula VIII

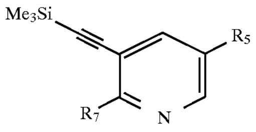

VIII wherein $R^5$ and $R^7$ are as defined above by reaction with bistributyltin oxide in an inert solvent such as tetrahydrofuran at a temperature between room temperature and the boiling point of the solvent in the presence of a catalyst such as tetrabutylammonium fluoride.

Compounds of formula VIII above may be obtained from compounds of formula IX

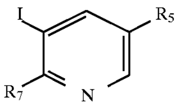

IX wherein $R^5$ and $R^7$ are as defined above, by reaction with trimethylsilylacetylene in an inert solvent such as triethylamine, tetrahydrofuran, dioxane, dimethylformamide or N-methylpyrrolininone at a temperature between room temperature and the boiling point of the solvent in the presence of Copper(I) iodide and catalyst such as $Pd(Ph_3P)_2Cl_2$ or $Pd(Ph_3P)_4$.

Compounds of formulae VI and IX may be obtained by known literature methods or obvious variations thereof.

It will be obvious to those skilled in the art that in some instances the reactions described cannot be effected in the presence of reactive intermediates incompatible with the reaction conditions. In such cases, the reactive substituent must first be derivatized via known per se methods to contain a suitable protective group, which can then be subsequently removed.

BIOLOGICAL PROPERTIES

The above described compounds of formula I possess inhibitory activity against HIV-1 reverse transcriptase. When administered in suitable dosage forms, they are useful in the prevention or treatment of AIDS, ARC and related disorders associated with HIV-1 infection. Another aspect of the invention, therefore, is a method for preventing or treating HIV-1 infection which comprises administering to a human being, exposed to or infected by HIV-1, a prophylactically or therapeutically effective amount of a novel compound of Formula 1 as described above.

The compounds of formula 1 may be administered in single or divided doses by the oral, parenteral or topical routes. A suitable oral dosage for a compound of formula 1 would be in the range of about 0.5 mg to 1 g per day. A preferred oral dosage for a compound of formula 1 would be in the range of about 100 mg to 800 mg per day. In parenteral formulations, a suitable dosage unit may contain from 0.1 to 250 mg of said compounds, preferably 1 mg to 200 mg, whereas for topical administration, formulations containing 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula 1 can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention can be administered by suppository.

As stated before, the compounds provided by the invention inhibit the enzymatic activity of HIV-1 RT. Based upon testing of these compounds, as described below, it is known that they inhibit the RNA-dependent DNA polymerase activity of HIV-1 RT.

Utilizing the Reverse Transcriptase (RT) Assay described below, compounds can be tested for their ability to inhibit the RNA-dependent DNA polymerase activity of HIV-1 RT. Certain specific compounds described in the Examples which appear below, were so tested. The results of this testing appear in Table I, below.

REVERSE TRANSCRIPTASE (RT) ASSAYS

Assay Theory:

Among the enzymes for which Human Immunodeficiency Virus (HIV-1) encodes is a reverse transcriptase (1), so-named because it transcribes a DNA copy from an RNA template. This activity can be quantitatively measured in a cell-free enzyme assay, which has been previously described (2), and is based upon the observation that reverse transcriptase is able to use a synthetic template [poly r(C) primed with oligo d(G)] to transcribe a radio-labelled, acid-precipitable DNA strand utilizing $^3$H-dGTP as a substrate. The assay described below utilizes the wild type (WT) enzyme, which is the predominant form of the enzyme observed in patients infected with HIV-1. Utilization of the mutant RT enzyme (Y181C, prepared by site-directed mutagenesis in which the tyrosine residue at codon 181 has been replaced by a cysteine residue) and analogous assay conditions allows compounds to be evaluated for their effectiveness at inhibiting this mutant enzyme.

Materials:

a) Preparation of the wild type enzyme

Reverse transcriptase enzyme from the LAV strain of Human Immunodeficiency Virus (HIV-1) (1) was isolated from the bacterial strain JM109 (3) expressing the DNA clone pBRTprtl+ (2) which is under the control of the lac promotor in the expression vector pIBI21 (4). An overnight culture grown in 2XYT medium (37° C., 225 rpm) (5) supplemented with 100 μ g/mL ampicillin for positive selection is inoculated at a 1:40 dilution into M9 medium supplemented with 10 μg /mL thiamine, 0.5% casamino acids, and 50 μg/mL ampicillin (5). The culture is incubated (37° C., 225 rpm) until it reaches an OD540 of 0.3–0.4. At that time the repressor inhibitor IPTG (isopropyl β-D-thiogalactopyranoside) is added to 0.5 mM, and the mixture is incubated for 2 additional hours. Bacteria are pelleted, resuspended in a 50 mM Tris, 0.6 mM EDTA, 0.375M NaCl buffer and digested by the addition of lysozyme (1 mg/mL) for 30 minutes on ice. The cells are lysed by the addition of 0.2% NP-40 and brought to 1M NaCl.

After removal of the insoluble debris by centrifugation, the protein is precipitated by the addition of 3 volumes of saturated aqueous ammonium sulfate. The enzyme is pelleted, resuspended in RT buffer (50 mM Tris pH 7.5, 1 mM EDTA, 5 mM DTT, 0.1% NP-40, 0.1M NaCl, and 50% glycerol), and stored at −70° C. for further use.

b) Composition of 2× concentrated stock reaction mixture

| Stock Reagent | 2 X Mix Concentration |
|---|---|
| 1M Tris pH 7.4 | 100 mM |
| 1M Dithiothreitol | 40 mM |
| 1M NaCl | 120 mM |
| 1% Nonidet P-40 | 0.1% |
| 1M MgCl | 4 mM |
| [poly r(C)/oligo d(G)](5:1) | 2 μg/mL |
| $^3$H-dGTP (81 μM) | 0.6 μM |

Assay Procedure:

The 2× concentrated stock reaction mixture is aliquoted and stored at −20° C. The mixture is stable and thawed for use in each assay. This enzyme assay has been adapted to a 96 well microtiter plate system, and has been previously described (6). Tris buffer (50 mM, pH 7.4), vehicle (solvent diluted to match the compound dilution), or compounds in vehicle are dispensed into 96-well microtiter plates (10 μL/well; 3 wells/compound). The HIV-1 RT enzyme is thawed, diluted in 50 mM Tris pH 7.4 so that fifteen μL of diluted enzyme contain 0.001 Unit (one unit is that amount of enzyme to transform 1 micromole of substrate per minute at 25° C.), and fifteen μL are dispensed per well. Twenty μL of 0.12–0.5M EDTA are added to the first three wells of the microtiter plate. EDTA chelates the Mg++ present and prevents reverse transcription. This group serves as background polymerization which is subtracted from all other groups. Twenty-five μl of the 2× reaction mixture are added to all wells and the assay is allowed to incubate at room temperature for 60 minutes. The assay is terminated by precipitating the DNA in each well with 50 μL of 10% trichloracetic acid (TCA) (10% w/v) in sodium pyrophosphate (1% w/v). The microtiter plate is incubated for 15 minutes at 4° C. and the precipitate is fixed onto #30 glass fiber paper (Schleicher & Schuell) using a Skatron semi-automatic harvester. The filters are then washed with additional TCA (5%) containing sodium pyrophosphate (1%), rinsed with aqueous ethanol (70%), dried, and transferred to scintillation vials (6). Each vial receives 2 mL of scintillation cocktail and is counted in a Beckman beta counter.

The calculation for percent inhibition is as follows:

$$\% \text{ inhibition} = \frac{CPM \text{ Mean Test Value} - CPM \text{ Mean Control Value} \times 100}{CPM \text{ Mean Control Value}}$$

References:

1. Benn, S., et al., *Science* 230:949, 1985
2. Farmerie, W. G. et. al., *Science* 236:305, 1987
3. Yanisch-Perron, C., Viera, J., and Messing, J., *Gene* 33:103, 1985
4. International Biotechnologies, Inc., New Haven, Conn. 06535
5. Maniatis, T, Fritsch, E. F., and J. Sambrook, eds. *Molecular Cloning: A Laboratory Manual,* Cold Spring Harbor Laboratory, 1982
6. Spira, T., et. al. *J. Clinical Microbiology,* 25:97, 1987.

TABLE 1

| Ex. No. | RT (WT) % inh. (1 μM) | RT (Y181C) % inh. (1 μM) | RT (L100I) % inh. (1 μM) | RT (K103N) % inh. (1 μM) | RT (P236L) % inh. (1 μM) |
|---|---|---|---|---|---|
| 1. | 98 | 53 | 81 | 73 | 99 |
| 2 | 97 | 41 | 80 | 55 | 98 |

EXAMPLES

The following examples further illustrate the present invention and will enable others skilled in the art to understand it more completely. It should be understood, however, that the invention is not limited to the particular examples given below.

Example 1

11-Ethyl-dipyrido[3,2-b:2',3'-f]azepine 2-Fluoro-3-(trimethlsilylethynyl)pyridine A mixture of 2-fluoro-3-iodopyridine (5 g), trimethylsilylacetylene (2.86 g) copper(I) iodide (0.015 g) and bis (triphenylphosphine)palladium dichloride (0.06 g) in a mixture of THF (20 mL) and triethylamine (30 mL) was stirred under argon for 4 hours. The solvents were evaporated and the residue was taken up in water/ethyl acetate. The organic phase was separated, dried and evaporated. Distillation of the residue gave 2-fluoro-3-(trimethylsilylethynyl)pyridine as an oil (4.10 g).

2-Fluoro-3-(tributylstannylethynyl)pyridine

A mixture of 2-fluoro-3-(trimethylsilylethynyl)pyridine (2.61 g), bistributyltin oxide (8.4 g) and tetrabutylammonium fluoride (3 drops) in dry tetrahydrofuran (100 mL) was heated at 50° C. for 5 hours. The solvent was evaporated and the residue was purified by chromatography over silica gel to give 2-fluoro-3-(tributylstannylethynyl)pyridine (3.04 g).

Z-2-Fluoro-3-(2-tributylstannylethenyl)pyridine

To a suspension of $Cp_2ZrHCl$ (2.58 g) in dry THF (50 mL) was added 2-fluoro-3-(tributylstannylethynyl)pyridine (2.05 g). After 2 hours the mixture was diluted with hexane and filtered through a short silica gel column. Evaporation of the solvents gave Z-2-fluoro-3-(2-tributylstannylethenyl) pyridine as an oil (1.72 g).

Z-1,2-di-(2-fluoropyridin-3-yl)ethylene

A mixture of Z-2-fluoro-3-(2-tributylstannylethenyl) pyridine (1.39 g), 2-fluoro-3-iodopyridine (0.75 g) and bis (triphenylphosphine)palladium dichloride (0.010 g) in toluene (20 mL) was refluxed under argon for 4 hours. Most of the solvent was evaporated and the residue was treated overnight with aqueous potassium fluoride. The organic phase was dried and evaporated to give Z-1,2-di-(2-fluoropyridinyl)ethylene as a solid which was recrystallized from hexane/ethyl acetate (0.47 g) mp 93°–95° C.

11-(p-Methoxybenzyl)dipyrido[3,2-b:2',3'-f]azepine

A mixture of Z-1,2-di-(2-fluoropyridinyl)ethylene (0.75 g) and p-methoxybenzylamine (1.41 g) was heated in a sealed test tube for 10 hours. The mixture was then fractionated over silica gel to give 11-(p-methoxybenzyl) dipyrido[3,2-b:2',3'-f]azepine (0.42 g) mp 124°–127° C.

Dipyrido[2,3-b:3',2'-f]azepine

A solution of 11-(p-methoxybenzyl)dipyrido[3,2-b:2',3'-f]azepine (0.158 g) in dichloromethane (20 mL) containing trifluoroacetic acid (0.22 g) was refluxed under argon for 4 hours. The mixture was basified with 10% aqueous potassium carbonate and the organic phase was separated, evaporated and fractionated over silica gel to give dipyrido[2,3-b:3',2'-f]azepine (0.075 g) mp 126°–129° C.

11-Ethyl-dipyrido[2,3-b:3',2'-f]azepine

To a solution of dipyrido[3,2-b:2',3'-f]azepine (0.195 g) in THF (20 mL) at room temperature under argon was added sodium hexamethyldisilazide (1M in THF, 2 mL). After 1 hour ethyl iodide was added and the mixture was stirred at room temperature for 4 hours. The solvent was then evaporated and the residue was chromatographed over silica gel to give 8-Ethyl-dipyrido[2,3-b:3',2'-f]azepine (0.145 g) mp 95°–97° C.

Example 2

11-Cyclopropyl-dipyrido[2,3-b:3',2'-f]azepine

A mixture of Z-1,2-di-(2-fluoropyridinyl)ethylene (0.436 g) and cyclopropylamine (2 g) was heated at 125° C. in a sealed tube for 12 hours. The mixture was cooled and fractionated directly over silica gel to give 11-cyclopropyl-dipyrido[2,3-b:3',2'-f]azepine (0.258 g), mp 184°–185° C.

EXAMPLE A

Capsules or Tablets

| A-1 | | A-2 | |
|---|---|---|---|
| Ingredient | Quantity | Ingredient | Quantity |
| Compound of Ex. 1 | 250 mg | Compound of Ex. 1 | 50 mg |
| Starch | 160 mg | Dicalcium Phosphate | 160 mg |
| Microcrys. Cellulose | 90 mg | Microcrys. Cellulose | 90 mg |
| Na Starch Glycolate | 10 mg | Stearic acid | 5 mg |
| Magnesium Stearate | 2 mg | Sodium Starch Glycolate | 10 mg |
| Fumed colloidal silica | 1 mg | Fumed colloidal silica | 1 mg |

The compound of Example 1 is blended into a powder mixture with the premixed excipient materials as identified above with the exception of the lubricant. The lubricant is then blended in and the resulting blend compressed into tablets or filled into hard gelatin capsules.

EXAMPLE B

Parenteral Solution

| Ingredient | Quantity |
|---|---|
| Compound of Example 1 | 500 mg |
| Tartaric acid | 1.5 g |
| Benzyl Alcohol | 0.1% by weight |
| Water for injection | q.s. to 100 mL |

The excipient materials are mixed with the water and thereafter the compound of Example 1 is added. Mixing is continued until the solution is clear. The pH of this solution is adjusted to 3.0 and is then filtered into the appropriate vials or ampoules and sterilized by autoclaving.

EXAMPLE C

Nasal Solutions

| Ingredient | Quantity |
|---|---|
| Compound of Example 1 | 100 mg |
| Citric acid | 1.92 g |
| Benzalkonium chloride | 0.025% by weight |
| EDTA | 0.1% by weight |
| Polyvinylalcohol | 10% by weight |
| Water | q.s. to 100 mL |

The excipient materials are mixed with the water and thereafter the compound of Example 1 is added and mixing is continued until the solution is clear. The pH of this solution is adjusted to 4.0 and is then filtered into the appropriate vials or ampoules.

We claim:

1. A compound of the formula I

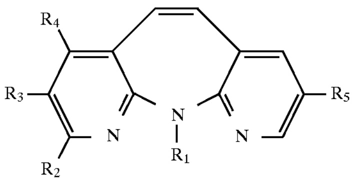

I wherein, $R^1$ is a hydrogen atom, alkyl of 1 to 4 carbon atoms, fluoroalkyl of 1 to 4 carbon atoms and 1 to 3 fluorine atoms, cycloalkyl of 3 to 6 carbon atoms, oxetanyl, thietanyl, tetrahydrofuranyl, tetrahydrothienyl, tetrahydropyranyl, tetrahydrothiopyranyl, alkenylmethyl or alkynylmethyl of 3 to 4 carbon atoms, alkyloxyalkyl or alkylthioalkyl of 2 to 3 carbon atoms, alkanoyl or alkyl(thiocarbonyl) of 2 to 5 carbon atoms, or cyanoalkyl of 2 to 3 carbon atoms;

$R^2$ is a hydrogen atom, alkyl of 1 to 6 carbon atoms, cycloalkyl of 3 to 6 carbon atoms, alkenyl or alkynyl of 2 to 6 carbon atoms, trihalomethyl, hydroxyalkyl of 1 to 6 carbon atoms, alkyloxy or alkylthio of 2 to 6 carbon atoms, alkyloxyalkyl or alkylthioalkyl of 2 to 6 carbon atoms, pyrrolidinyl, pyrrolinyl, piperidinyl, mono- or di-alkylamnino wherein each alkyl moiety contains 1 to 3 carbon atoms, halogen, cyano, nitro, or carboxyl, aryl (wherein aryl is phenyl, pyridinyl, thienyl, furanyl, pyrrolyl, imidazolyl, pyrazolyl, oxazolyl, isoxazolyl, thiazolyl or isothiazolyl) which is either unsubstituted or substituted by hydroxyl, amino, halogen, alkyl or alkyloxy of 1 to 3 carbon atoms:

$R^3$ is a hydrogen atom, methyl or halogen;

$R^4$ is a hydrogen atom, methyl, ethyl or halogen; and, $R^5$ is a hydrogen atom, hydroxy, amino, hydroxymethyl or aminomethyl;

or a pharmaceutically acceptable salt thereof.

2. A compound of formula I as set forth in claim 1, wherein, $R^1$ is alkyl of 1 to 3 carbon atoms or cycloalkyl of 3 to 4 carbon atoms $R^2$ is a hydrogen atom, methyl, trihalomethyl, methoxy, pyrrolidinyl, pyrrolinyl, piperidinyl, dimethylamino, halogen, cyano, nitro or aryl (wherein aryl is phenyl, pyridinyl, thienyl, furanyl, pyrrolyl, imidazolyl, pyrazolyl, oxazolyl, isoxazolyl, thiazolyl or isothiazolyl) which is either unsubstituted or substituted by methyl, methoxy, hydroxyl, amino, or halogen;

$R^3$ is a hydrogen atom, methyl, chloro or bromo;

$R^4$ is hydrogen or methyl; and, $R^5$ is a hydrogen atom;

or a pharmaceutically acceptable salt thereof.

3. A compound of formula I, as set forth in claim 1, wherein, $R^1$ is ethyl or cyclopropyl;

$R^2$ is hydrogen, chloro, or pyrazolyl; and, $R^3$, $R^4$, $R^5$ are hydrogen.

4. A compound selected from the group consisting of:

11-Ethyl-dipyrido[2,3-b:3',2'-f]azepine;

11-Cyclopropyl-dipyrido[2,3-b:3',2'-f]azepine;

and the pharmaceutically acceptable salts thereof.

5. A method for treating HIV-1 infection which comprises administering, to a human being exposed to or infected by HIV-1, therapeutically effective amount of a compound of formula I, as set forth in claim 1, 2, 3 or 4, or a pharmaceutically acceptable salt thereof.

6. A pharmaceutical composition suitable for treating HIV-1 infection which comprises therapeutically effective amount of a compound of formula I, as set forth in claim 1, 2, 3 or 4, or a pharmaceutically acceptable salt thereof, and a pharmaceutically acceptable carrier.

* * * * *